United States Patent
Head

(10) Patent No.: US 9,645,089 B1
(45) Date of Patent: May 9, 2017

(54) METHOD FOR DETERMINING OPTODE QUALITY

(71) Applicant: PRECISION MEASUREMENT ENGINEERING, INC., Vista, CA (US)

(72) Inventor: Michael Jay Head, Encinitas, CA (US)

(73) Assignee: PRECISION MEASUREMENT ENGINEERING, INC., Vista, CA (US)

( * ) Notice: Subject to any disclaimer, the term of this patent is extended or adjusted under 35 U.S.C. 154(b) by 956 days.

(21) Appl. No.: 13/764,683

(22) Filed: Feb. 11, 2013

(51) Int. Cl.
  *G01N 21/00* (2006.01)
  *G01N 21/77* (2006.01)
(52) U.S. Cl.
  CPC .................. *G01N 21/77* (2013.01)
(58) Field of Classification Search
  CPC ...................................... G01N 21/77

USPC .......................................................... 702/25
See application file for complete search history.

(56) References Cited

U.S. PATENT DOCUMENTS

| | | | | |
|---|---|---|---|---|
| 6,360,582 | B1 * | 3/2002 | Chelvayohan | G01N 21/274 250/339.09 |
| 8,922,777 | B2 * | 12/2014 | Shemer | G01N 21/274 345/19 |
| 2002/0023479 | A1 * | 2/2002 | Burge | G01N 33/18 73/1.01 |
| 2015/0011010 | A1 * | 1/2015 | Steinbrueck | G01N 21/643 436/163 |

\* cited by examiner

*Primary Examiner* — Ricky Ngon
(74) *Attorney, Agent, or Firm* — One LLP

(57) ABSTRACT

An improved luminescent optode is disclosed that is capable of conducting a self-test to determine the quality of the optode's measurement of the concentration of a quenching molecule in a fluid, along with a method for conducting the self-test.

20 Claims, 5 Drawing Sheets

METHOD FOR DETERMINING OPTODE QUALITY

BACKGROUND OF THE INVENTION

The present invention relates generally to the field of optodes. Optodes are optical sensor devices that optically measure the concentration of a specific substance within a fluid (a liquid or a gas), usually with the aid of a chemical transducer. More particularly, the invention is directed to a method, and to an improved optode that implements the method, whereby the optode is capable of conducting a self-test of its measurement quality, to determine whether the optode is no longer providing accurate measurements. The method and the improved optode are discussed primarily in connection with the measurement of dissolved oxygen in water, but it should be understood that they could also be used to measure other chemicals in other types of fluids.

Accurate measurement of the concentration of dissolved oxygen in a body of water is important for a variety of reasons. For example, low oxygen concentrations are a common water quality problem downstream of hydropower facilities. Many hydropower operators measure oxygen concentrations to insure that they are within regulatory compliance.

A luminescence-based optode typically includes a sensor cap that is coated with a luminescent material within a polymer matrix (the chemical transducer), circuitry to illuminate this material, and circuitry to detect the material's luminescent emission. The optode is designed such that blue light (the excitation light) from a light source strikes the luminescent material on the optode cap. Photons of this blue light collide with electrons of the luminescent material, providing the electrons with sufficient energy to boost (excite) them into higher energy orbits. These electrons cannot remain in the excited state indefinitely and, over time, return to the initial, unexcited state, losing the excitation energy. For the purposes of this invention there are two ways this energy is lost. The first is that the energy is emitted as photons of red light. The second is that the energy is lost, without emission of photos, by collision with a nearby quenching molecule. Both types of energy loss can and do occur at the same time. Only a fraction of an excited population of electrons will be quenched, leaving the remaining electrons to return to the unexcited state by emitting red light. Thus, the properties of the emitted light, such as its intensity and the lifetime of the emission, will change in a way that depends upon the concentration of quenching molecules. A photo detector and electrical circuits are used to measure characteristics of the emitted light. Optical filters are used to prevent blue excitation light from reaching this photo detector, so emission light can be measured at the same time as the material is receiving excitation light.

The phenomenon of quenching forms the basis for two common methods for determining the concentration of the "quenching" molecules, such as oxygen. The first method uses intensity-based measurements wherein the intensity of emission is measured and declines as the concentration of the quencher increases. The second method uses lifetime-based measurements wherein the characteristic time of decay of emission is measured and becomes shorter as the concentration of the quencher increases. Until the present invention, optodes have generally used only one of these two methods.

Optodes that use the intensity-based method operate by measuring the ratio of the intensity of excitation to that of the intensity of emission. Quencher molecules (e.g., oxygen) deactivate a fraction of the excited electrons and so reduce the number of electrons that emit and therefore reduce the emission intensity relative to the excitation intensity.

The optode is calibrated by exposing the luminescent material to different temperatures and concentrations of the quencher and measuring the resulting intensity ratio. An interpolation function $f_i$ is determined from the measurements to provide a mathematical expression that describes the functional relationship between the concentration of the quenching molecule, the intensity of the emission, the intensity of the excitation, and the temperature of the luminescent material, as follows:

$$[C] = f_i(L_{em}/L_{ex}, T)$$

where
[C] is the concentration of the quencher,
$L_{em}$ is the intensity of emission,
$L_{ex}$ is the intensity of excitation, and
T is the temperature of the material.

This intensity-based method is relatively simple to implement but it is known to suffer from defects. Often, for cost and convenience reasons, only $L_{em}$ is monitored, and $L_{ex}$ is assumed constant. Common sources of $L_{ex}$, such as light emitting diodes (LEDs), gradually loose intensity over time. In that case, variations in $L_{ex}$ will be mistakenly interpreted as variations in $L_{em}$, and the measurement of [C] will be inaccurate. Also, in practice, $f_i$ does not completely describe the response of the luminescent material. For example, $f_i$ is known to change as a function of the amount and duration of the excitation light, an effect that is known as "photo bleaching" of the luminescent material. The resulting changes in the true $f_i$ relative to the $f_i$ that was determined by calibrating the optode, result in inaccurate measurement of [C]. Finally, if variations in the optical path occur that change the intensity of excitation or emission light individually, then $L_{em}/L_{ex}$ will change and the measurement of [C] will be inaccurate. Such variations in the optical path can be caused by condensation of water within the optics or movement of the optics due to external stresses or rough handling of the optode.

Optodes that use the lifetime-based method operate on the principle that in the quenched luminescent material an impulse excitation creates a population of excited electrons that leave the excited state at an exponentially decaying rate, with the exponent described as the 'characteristic time'. Quencher molecules (e.g., oxygen) deactivate a fraction of the excited electrons and so reduce the number of electrons that emit and, therefore, reduce the characteristic time of the emission. It can also be shown that a system of this type will exhibit a response to the application of an excitation light having sinusoidally varying intensity, by producing an emission light having a sinusoidally varying intensity at the same frequency as the excitation light, but delayed by a specific amount of time, a 'phase shift'. The measurement of phase shift is a common method used within optodes for determining the characteristic time.

The optode is calibrated by exposing the luminescent material to different temperatures and concentrations of the quencher and measuring the resulting characteristic time. An interpolation function $f_t$ is determined from the measurements to provide a mathematical expression that describes the functional relationship between the concentration of the quenching molecule, the characteristic time (or phase angle) of emission, and the temperature of the luminescent material, as follows:

$$[C] = f_t(t, T)$$

where

[C] is the concentration of the quencher, t is the characteristic time of emission, and T is the temperature of the material.

This is a more complex measurement to make, and requires more complex electronics, but the lifetime-based measurement method does not suffer dramatically from the problems of the intensity-based measurement method described above. There is one subtle problem, however. In practice, the measurement of the characteristic time becomes more difficult as the emission intensity declines (for any of the reasons discussed in the intensity-based method above). In general, the measurement of characteristic time exhibits good stability over ranges of high intensity with problems occurring at low intensity. The lifetime-based method, although better than intensity-based, is not completely insensitive to intensity. Despite this subtle problem, many commercial sources of oxygen optodes use this lifetime-based method to evaluate the quenching effect and to determine the oxygen concentration.

Regardless of which method an optode implements—the intensity-based method or the lifetime-based method—the quality of the measurements made by the optode optode will eventually degrade. It is important that an optode not be used to collect data after its measurement quality has degraded below an acceptable level because incorrect measurements can lead to incorrect decisions. Continuing the example above, an incorrect measurement of oxygen could lead a hydropower operator to believe that they are not compliant with regulations and cause them unnecessary expense.

Normally, one cannot know whether an optode is making quality measurements without removing the optode from service and testing it. It would be beneficial and advantageous to have a way to determine when the quality of an optode's measurements has degraded, without having to remove the optode from service to test the optode.

BRIEF SUMMARY OF THE INVENTION

In a basic aspect, the present invention is a method for determining the quality of an optode measurement of the concentration of a quenching molecule in a fluid (such as, for example, molecular oxygen in a body of water).

The method is implemented by an improved luminescent optode that has all the necessary components to perform (a) an intensity-based determination of the concentration of the quenching molecule; (b) a lifetime-based determination of the concentration of the quenching molecule; and (c) a measurement of the temperature of the luminescent material. The functions $f_i$ and $f_t$ described above, can be determined from measurements collected during a single calibration. The values of t, $L_{em}/L_{ex}$ and T can be measured by the optode during subsequent use of the optode.

These measurements can be used together with $f_i$ and $f_t$ to produce two estimates of [C]. These estimates should agree if the optode is providing quality measurements. Disagreement between these two estimates indicates that the measurement quality has become questionable, and the optode can be removed from service.

A threshold 'quality factor' can be determined based on the two estimates of [C], using any of a variety of different techniques. For example, the quality factor may be expressed as a ratio of the two estimates of [C], or as a percentage difference between the two estimates. So, for example, the quality factor may be set to flag any optode for which the first estimate of [C] differs from the second estimate of [C] by more than 5%, or any other chosen value.

This quality factor can then be compared to a predetermined maximum or minimum quality factor, and can be used to trigger an alarm to indicate when a sensor malfunction has occurred or to indicate when the sensor requires re-calibration or other service.

The inventive method generally comprises the steps of:

1) determining a mathematical relation between the intensity of light emitted from an excited luminescent material into which the quenching material has been diffused, the concentration of the quenching material, and the temperature of the luminescent material (i.e., calibrating the intensity and temperature versus dissolved oxygen concentration [C] relationship);

2) determining a mathematical relation between the characteristic time of light emitted from the excited luminescent material into which the quenching material has been diffused, the concentration of the quenching material and temperature of the luminescent material (i.e., calibrating the characteristic time (or phase angle) and temperature versus dissolved oxygen concentration [C] relationship);

3) exposing the luminescent material to a particular concentration of the quenching material and measuring the temperature, T, of the excited luminescent material, the intensity of the light emitted from the excited luminescent material, $L_{em}/L_{ex}$, and the fluorescent lifetime of the light emitted from the excited luminescent material, t; and, 4) using the mathematical relations determined in step (1) and step (2) to calculate measurement parameters using the quantities measured in step (3); and 5) comparing the calculated measurement parameters using a predetermined quality factor, to determine whether the optode's measurement quality has degraded beyond an acceptable level.

The invention also includes devices for performing the above-described methods, including an optode with a microprocessor circuit that is cable of controlling the various optode components and directing the optode components to collect and process the data according to the method.

In another aspect of the invention, steps (1) and (2) (the calibration steps) are performed in a controlled calibration vessel and step (3) is performed in a body of fluid that is being tested to determine the concentration of the quenching molecule in the fluid.

Another embodiment includes the further step, following steps (1) and (2), of combining the optode with other optodes to form a string of spaced-apart optodes, and immersing the string of optodes into the body of fluid (such as a body of water). The method also comprises the further steps of (a) performing the self-test method on a plurality of the optodes on the string; and (b) sending an alarm signal from any of the plurality of optodes for which the differences between the measurement parameters exceeded the predetermined quality factor, to alert a user that a particular optode's measurement quality might have degraded beyond an acceptable level.

Another embodiment of the invention comprises (a) operating a plurality of optodes that perform the above-described self-diagnostic method; (b) testing each optode in accordance with the inventive self-test diagnostic method; and (c) removing from service any optodes for which the self-test indicates a problem with the optode's measurement quality.

DETAILED DESCRIPTION OF THE INVENTION

As discussed above, the present invention relates generally to luminescence-based optodes for measuring the concentration of a quenching molecule in a fluid. The following detailed description focuses primarily on the measurement of oxygen in water, but the measurement of some other quenching molecule in a different fluid will be substantially the same.

Figure 1:
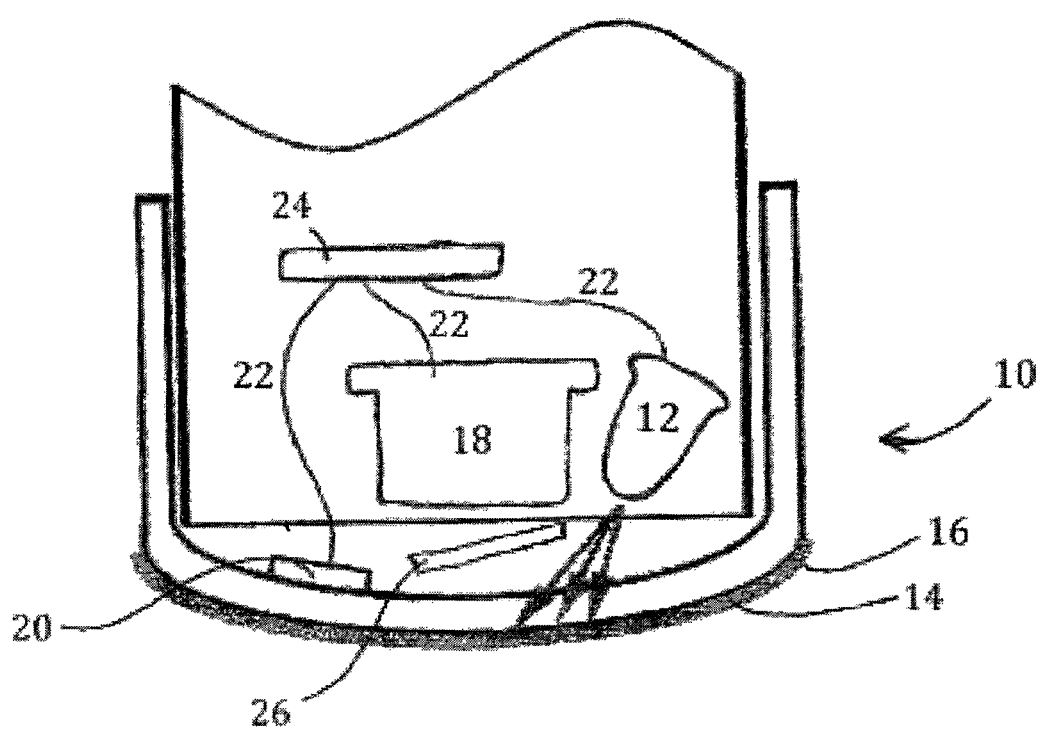
FIG. 1 of the drawing is a schematic diagram showing various components of a typical fluorescence-based optode.

As shown in FIG. 1, a luminescent optode 10 typically comprises a light source 12 (shown as an LED in the figure) that provides blue excitation light to a luminescent material 14 within a polymer matrix 16. The optode 10 also includes a photo-detector 18 (shown as a photo diode in the figure) for detecting and measuring light emitted from the luminescent material 14. The optode 10 also includes a thermometer 20 (shown as a thermistor in the figure), and associated electrical conductors 22 (wires) for connecting the aforementioned components into a microprocessor control circuit 24. The control circuit 24 is adapted and programmed to control the components and to make the various measurements and to perform the various calculations described herein. An optical filter 26 is included between the luminescent material and the photo-detector, to control the light that is detected by the photo-detector, to block blue excitation light from being detected, while permitting red emission light to be detected.

Figure 2:
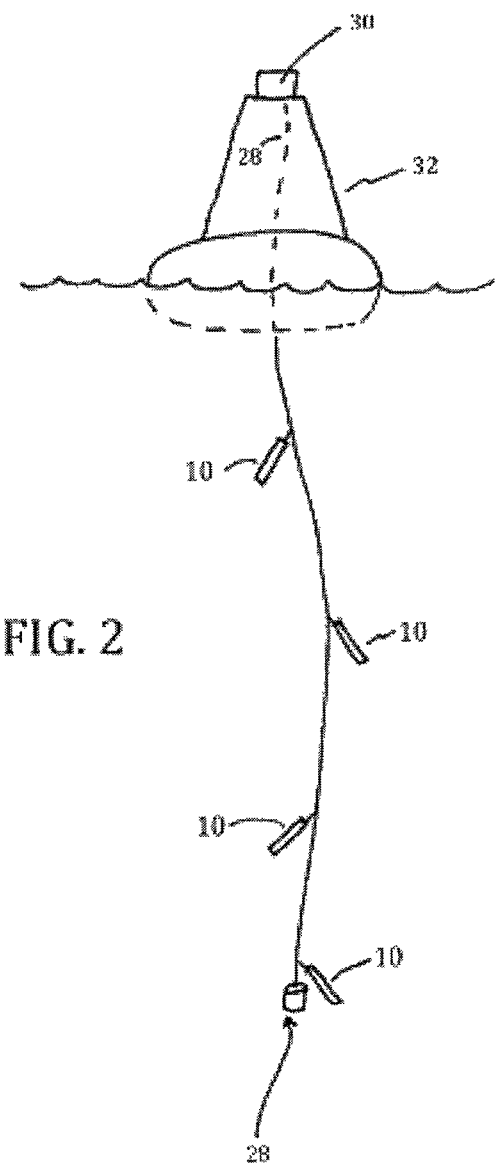
FIG. 2 of the drawing is a schematic diagram showing various components of a system for measuring, storing and transmitting data from a plurality of optodes or from a limited number of optodes operated at multiple different locations.

As shown in FIG. 2, one or more optodes 10 can be used to measure the concentration of dissolved oxygen (or another quenching molecule) at one or more locations or depths within a body of water. A plurality of optodes 10 can be combined together to form a string 28 of separate optodes 10. In one embodiment, each of the optode's in the string of optodes communicates with a single base station 30 that is located, for example, on a buoy or other vessel 32 from which the string of optodes is suspended into the water. The base station can collect and process data from the various optodes.

In another embodiment, the data can be processed by the microprocessor control circuit onboard each optode. The data from the various measurements can also be stored onboard the optode, for example, by storing the data on a storage device such as an SD card, or the data can be transmitted from the optode, through wires or via a radio signal or other type of wireless transmission, to a collection point, such as the base station or a central computer.

Figure 3:
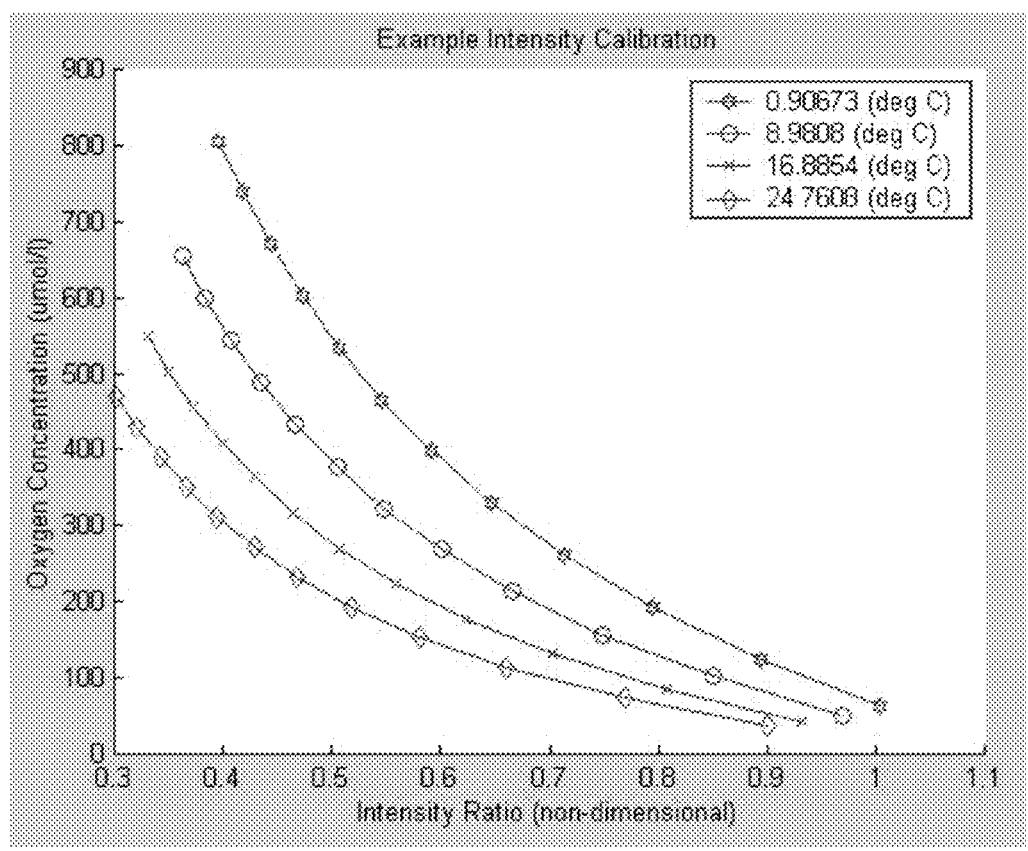
FIG. 3 of the drawing is an exemplary graph of data points and calibration curves for intensity versus dissolved oxygen concentration.

As shown in FIG. 3, the optode is calibrated at various concentrations [C] and at various temperatures, $T_1$, $T_2$, $T_3$ and $T_4$, giving measurements of intensity. An interpolation function $f_i$ is mathematically generated from these measurements.

Figure 4:
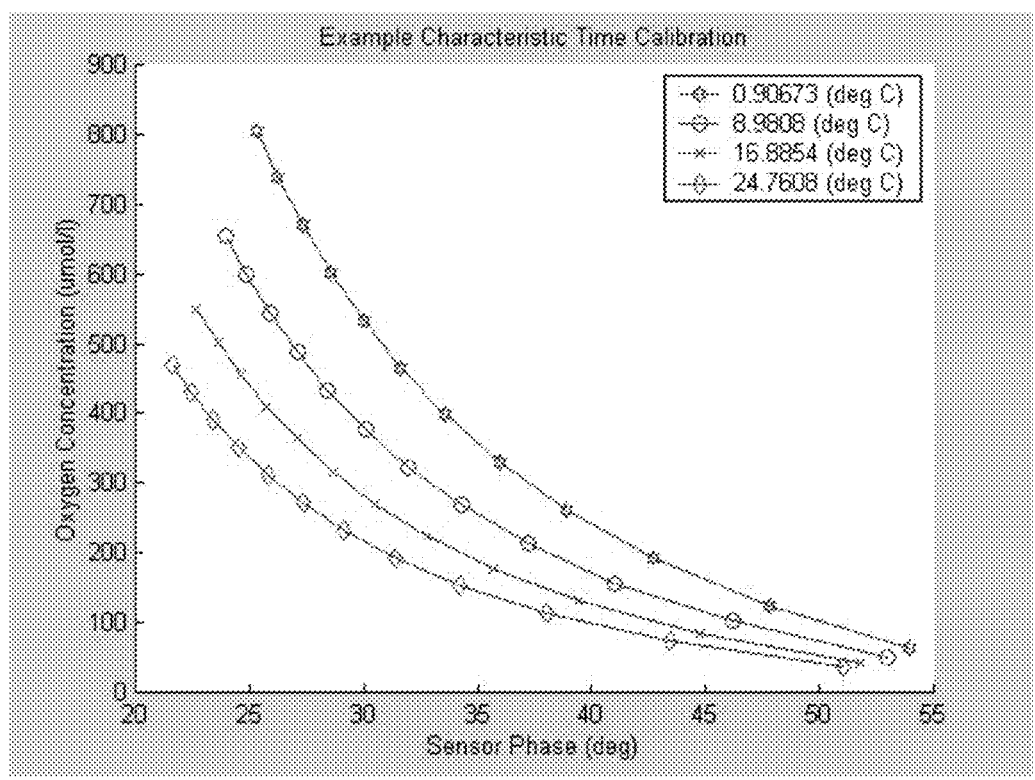
FIG. 4 of the drawing is an exemplary graph of data points and calibration curves for characteristic time (shown as phase shift in the figure) versus dissolved oxygen concentration.

As shown in FIG. 4, the optode is also calibrated at various concentrations [C] and at various temperatures $T_1$, $T_2$, $T_3$ and $T_4$, giving measurements of characteristic time, t (shown as phase shift in the figure). An interpolation function $f_t$ is mathematically generated from these measurements.

One step of the present invention involves determining a mathematical relation, $[C]=f_i(L_{em}/L_{ex},T)$, between the intensity of light emitted from an excited luminescent material into which the quenching material has been diffused and the concentration of the quenching material, at a variety of different temperatures (i.e., calibrating intensity versus dissolved oxygen concentration ([C]) at a variety of different temperatures).

Figure 5:
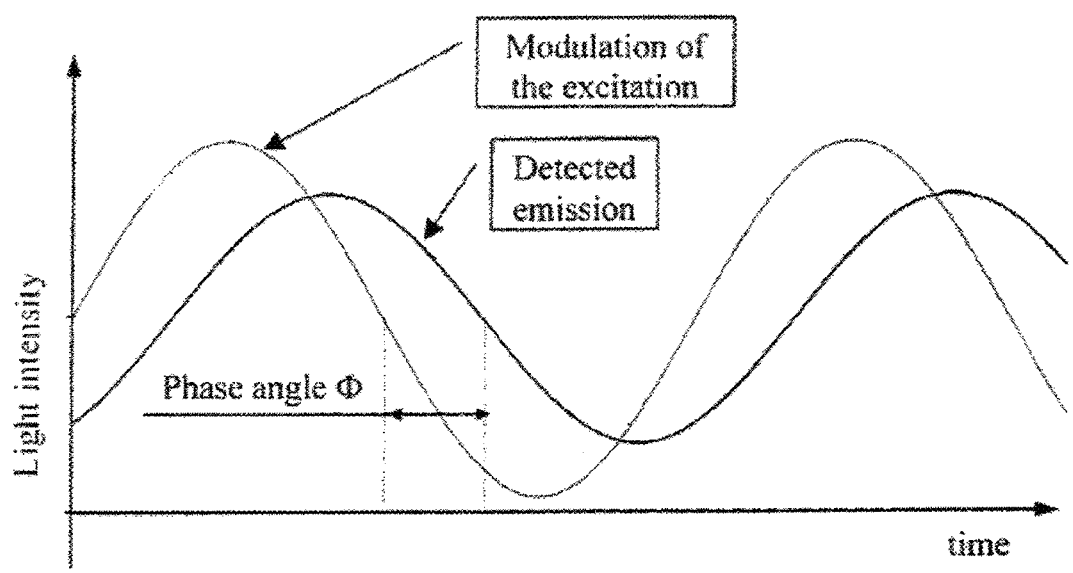
FIG. 5 of the drawing is illustrates the concepts of phase shift and illumination time in a luminescent optode.

Another step of the invention involves determining a mathematical relation, $[C]=f_t(t, T)$ between the characteristic time of the emitted light and the concentration of the quenching material and temperature of the luminescent material, at a variety of different temperatures (i.e., calibrating the characteristic time (or phase shift) versus dissolved oxygen concentration ([C]) at a variety of different temperatures). The phase shift or characteristic time is illustrated in FIG. 5.

The functions $f_i$ and $f_t$, in these steps can be conveniently determined from measurements collected during a single calibration procedure but can also be individually determined from separate calibrations. In either case the calibration method is the same. Calibration of an oxygen optode consists of the experiment of exposing the optode to a number of different oxygen concentrations at a number of different temperatures, and recording the oxygen concentration [C], the temperature T, the intensity ratio $L_{em}/L_{ex}$, the characteristic time t. From these data values, the functional relationships $f_i$ and $f_t$ can be determined using any of a variety of well known mathematical techniques.

Calibration experiments can be performed in different ways. One common way is to place the optode into a temperature controlled bath of water and to create different concentrations of oxygen dissolved within the water by bubbling air, oxygen, or nitrogen thru the water. Oxygen concentration is determined by a reference, either another sensor of some sort or by chemical assay techniques. Temperature is determined by a reference thermometer or by the optode's thermometer. At specific times the reference measurements of oxygen, [C], temperature, T, and the optode measurements of intensity, $L_{em}/L_{ex}$, and characteristic time, t, are obtained.

Optode measurements are obtained by direct communication with the optode at the time of the measurement, or the optode may internally record the measured values and those obtained at the end of the experiment. As time passes a group of measurement points are obtained: $<[C_1], T_1, L_{em1}/L_{ex}, t_1>$, $<[C_2], T_2, L_{em2}/L_{ex}, t_2>$, $<[C_3], T_3, L_{em3}/L_{ex}, t_3>$, and so on.

The activity of determining $f_i$ and $f_t$ consists of selecting an appropriate mathematical expression containing unknown constant values $P_X$, such as the polynomial $Y=P_0+P_1+P_2X+P_3X^2$ and then determining the constants $P_0$, $P_1$, $P_2$ and $P_3$, such that the mathematical expression represents the true $f_i$ and $f_t$ in some optimal way. This activity is often referred to as 'fitting measurements by the method of least squares'.

Another step of the inventive method involves exposing the luminescent material to a particular unknown concentration of the quenching material and measuring the temperature of the luminescent material, T, the intensity of the light emitted from the excited luminescent material, $L_{em}/L_{ex}$, and the characteristic time, t, of the light emitted from the excited luminescent material. This step occurs during actual use of the optode as a sensor.

Another step of the inventive method involves using these measurements, T, $L_{em}/L_{ex}$, t, together with the mathematical relationships, $[C]=f_i(L_{em}/L_{ex}, T)$ and $[C]=f_t(t, T)$ to produce two estimates of [C]. These estimates should agree if the optode is providing quality measurements. Disagreement between these two estimates indicates that the measurement quality has become questionable, and the optode can be removed from service. A threshold 'quality factor' can be determined based on the two factors, using any of a variety of different techniques. For example, the quality factor may be expressed as a ratio of the two estimates, or as a percentage difference between the two estimates. So, for example, the quality factor may be set to flag any optode for which the first estimate of [C] differs from the second estimate of [C] by more than 5%, or any other chosen value.

In the preceding paragraph, measurement quality is determined by the comparison of two concentration estimates. However the quality factor can also be expressed in different ways, with other expressions giving additional insight into the operation of the optode. For example it was previously mentioned that the optode is expected to gradually lose intensity due to photo bleaching of the luminescent material or other factors. A useful quality factor could be determined by determining the concentration estimate from the measured characteristic time and temperature and then using this concentration together with a reciprocal $f_i$ to determine the intensity at calibration time that would have produced the measured concentration. The measured intensity can then be compared to this calibration-intensity to give an estimate of photo bleaching. Mathematically this is be expressed as:

$$Q=(L_{em}/L_{ex})m/f_i^{-1}(f_t(t_m,T_m),T_m)$$

where

Q is the quality, $(L_{em}/L_{ex})_m$ is the measured intensity of emission, $T_m$ is the temperature of the luminescent material, and $t_m$ is the measured characteristic time of emission.

Q might also be expressed as a difference, percentage difference, or some other form of comparison of $(L_{em}/L_{ex})_m$ and $f_i^{-1}(f_t(t_m,T_m),T_m)$.

In a similar way the characteristic lifetime at calibration could be compared to the measured characteristic lifetime. Mathematically this is expressed as:

$$Q=t_m/f_t^{-1}(f_i((L_{em}/L_{ex})_m,T_m),T_m)$$

where

Q is the quality, $(L_{em}/L_{ex})_m$ is the measured intensity of emission, $T_m$ is the temperature of the luminescent material, and $t_m$ is the measured characteristic time of emission.

Q might also be expressed as a difference, percentage difference, or some other form of comparison of $t_m$ and $f_t^{-1}(f_i((L_{em}/L_{ex})_m,T_m),T_m)$.

The invention also includes a device that implements the method described above. The device is similar to a regular optode device designed to operate under only the first (intensity-based) mode or under only the second (lifetime-based) mode, in terms of the arrangement of its light source, photo detector, thermometer, and the sensor cap coated with a luminescent material within a polymer matrix. However, the on-board circuit that controls the optode and its measurements is very different.

In particular, the on-board control circuit is adapted and designed to control the electronics and to gather and manipulate the data measured by the optode, in the manner discussed above. The data from the various measurements can be stored onboard the optode, for example, by storing the data on a storage device such as an SD card, or the data can be transmitted from the optode, via a radio signal or other type of wireless transmission, to a collection point, such as a base station or central computer. The controller circuit can also instruct the optode to signal an audible alarm or to transmit an alarm to a base station or central computer, if the quality factor is exceeded.

While the principles of the disclosure have been illustrated and explained in relation to the exemplary embodiments shown and described herein, the principles of the disclosure are not limited thereto and may be changed and modified without departing from the scope and spirit of the invention as defined in the claims.

What is claimed is:

1. A computer implemented method for determining the quality of a first optode's measurement of the concentration of a quenching material in a fluid, comprising:

instructions stored in a non-transitory computer-readable storage medium that, when executed by a processor, perform the steps of:

(a) calibrating the optode by performing at least one measurement to determine a first mathematical relation between:

(i) a first intensity of light emitted from an excited luminescent material in the fluid containing the diffused quenching material; and (ii) a first concentration of the quenching material in the fluid, for at least one temperature T1 of the luminescent material;

(b) calibrating the optode by performing at least one measurement to determine a second mathematical relation between:

(iii) a first fluorescence lifetime of light emitted from the excited luminescent material; and (iv) the first concentration of the quenching material in the fluid for at least the temperature T1 of the excited luminescent material;

(c) exposing the excited luminescent material to a second concentration of the quenching material in the fluid at a temperature T2 and measuring values of:

(v) a second intensity of light emitted from the excited luminescent material; and (vi) a second fluorescence lifetime of light emitted from the excited luminescent material;

(d) using the first mathematical relation determined in step (a) and the second mathematical relation determined in step (b) to calculate a value of at least one measurement parameter using temperature T2 and at least one of the measured second intensity of light and the second fluorescence lifetime; and comparing the calculated value with the measured value of at least one of the second intensity of light and the second fluorescence lifetime measured in step (c) to identify any differences between the calculated value and the measured values; and (e) determining whether any differences between the calculated value and measured values exceed a predetermined quality factor threshold, indicating that the optode's actual measurement quality has degraded and if any differences between the calculated value and the measured values exceed the predetermined quality factor threshold, alerting a user.

2. The method of claim 1, wherein steps (a) and (b) are performed in a controlled calibration vessel holding a first body of the fluid containing the diffused quenching material at the first concentration and step (c) is performed in a second body of the fluid that is being tested to determine the second concentration of the diffused quenching material in the second body of the fluid.

3. The method of claim 2, wherein the fluid is water and the quenching material is oxygen.

4. The method of claim 3, comprising the further step, following steps (a) and (b), of:
  combining the first optode with at least one additional optode to form a string of spaced-apart optodes and immersing the string of optodes into the fluid.

5. The method of claim 3, further comprising the steps of:
  connecting the first optode with additional optodes on a string such that they are spaced apart;
  performing the method of claim 1 on each of the plurality of optodes on the string; and
  wherein alerting a user further comprises: generating and transmitting an individual alarm signal for any of the plurality of optodes for which the differences between the calculated value and measured values exceed the predetermined quality factor threshold, wherein the alarm signal alerts a user of the string that the individual optode's measurement quality has degraded.

6. An apparatus for measuring a concentration of diffused quenching molecules in a body of fluid, comprising:
  a plurality of luminescent optodes connected in a string for immersion into the body of fluid, wherein each of the plurality of luminescent optodes is operable to communicate with a common base station and each of the plurality of luminescent optodes is adapted to perform the computer implemented method of claim 1.

7. The computer implemented method of claim 1, wherein alerting the user further comprises signaling the user using an audible alarm.

8. The computer implemented method of claim 1, wherein alerting the user further comprises transmitting an alarm to a wirelessly connected base station.

9. The computer implemented method of claim 1, wherein alerting the user further comprises transmitting an alarm to a base station via a wired connection.

10. The computer implemented method of claim 1, wherein alerting the user further comprises indicating a sensor malfunction.

11. The computer implemented method of claim 1, wherein alerting the user further comprises indicating the first optode requires re-calibration.

12. The computer implemented method of claim 1, wherein the exposing and measuring values in step (c) are performed simultaneously.

13. An improved luminescent optode sensor, comprising:
  (a) a sensor cap that is coated with a luminescent material within a polymer matrix;
  (b) a light source for illuminating the luminescent material, causing the luminescent material to become excited;
  (c) a sensor for detecting the excited luminescent material's light emission; and
  (d) a microprocessor control circuit for controlling the light source and the optode sensor, the control circuit being further adapted to:
    (1) store, in non-transitory computer readable memory, calibration information reflecting a first mathematical relationship between:
      (i) a measured first intensity of light emitted from the excited luminescent material in a fluid containing a diffused quenching material; and
      (ii) a measured first concentration of the quenching material in the fluid, for at least one measured temperature T1 of the excited luminescent material;
    (2) store, in non-transitory computer readable memory, calibration information reflecting a second mathematical relationship between:
      (iii) a measured first fluorescence lifetime of light emitted from the excited luminescent material; and
      (iv) the measured first concentration of the diffused quenching material in the fluid, for at least the measured temperature T1 of the excited luminescent material;
    (3) upon exposure of the luminescent material to a second concentration of the quenching material diffused in the fluid at a temperature T2, measure a second intensity of light emitted from the excited luminescent material and a second fluorescent lifetime of light emitted from the excited luminescent material;
    (4) use the first mathematical relationship described in (d)(1) and the second mathematical relationship in (d)(2) and the measured second intensity of light emitted from the excited luminescent material and the measured second fluorescent lifetime of light emitted from the excited luminescent material described in (d)(3) to calculate measurement parameter values;
    (5) compare the measurement parameter values to determine a quality factor reflecting the quality of the measured second intensity of light emitted from the excited luminescent material and the measured second fluorescent lifetime of the light emitted from the excited luminescent material made by the optode; and
    (6) determine whether the quality factor exceeds a predetermined threshold and if the quality factor exceeds the predetermined threshold, generating a user alert.

14. The improved luminescent optode sensor of claim 13, wherein the sensor for detecting the excited luminescent material's light emission further comprises:
  a photo detector.

15. The improved luminescent optode sensor of claim 13, further comprising a thermometer.

16. The improved luminescent optode sensor of claim 13, further comprising a wireless transceiver.

17. The improved luminescent optode sensor of claim 13, wherein the polymer matrix is a chemical transducer.

18. The improved luminescent optode sensor of claim 13, wherein the light source emits blue light.

19. The improved luminescent optode sensor of claim 13, further comprising:
  at least one optical filter to prevent light from the light source from reaching the sensor.

20. The improved luminescent optode sensor of claim 13, wherein the light source is an LED.

* * * * *